United States Patent [19]

Gjerde et al.

[11] Patent Number: 5,149,661
[45] Date of Patent: Sep. 22, 1992

[54] FLUID ANALYSIS WITH PARTICULATE REAGENT SUSPENSION

[75] Inventors: Douglas T. Gjerde, Saratoga, Calif.; James V. Benson, Reno, Nev.

[73] Assignee: Sarasep, Inc., Saratoga, Calif.

[21] Appl. No.: 357,514

[22] Filed: May 26, 1989

Related U.S. Application Data

[63] Continuation-in-part of Ser. No. 204,073, Jun. 8, 1988, abandoned.

[51] Int. Cl.$^5$ .......................... G01N 1/18; G01N 35/08
[52] U.S. Cl. ........................................ 436/178; 436/52; 436/533; 436/534; 422/69
[58] Field of Search .............. 422/70, 145, 213, 211, 422/69; 436/533, 534, 541, 52, 150, 806, 178; 324/493

[56] References Cited

U.S. PATENT DOCUMENTS

| | | | |
|---|---|---|---|
| 3,246,759 | 4/1966 | Matalon | 210/96 |
| 3,271,672 | 9/1966 | Henderson | 324/71 |
| 3,536,450 | 10/1970 | Dus et al. | 23/253 |
| 3,926,559 | 12/1975 | Stevens | 23/230 |
| 4,002,428 | 1/1977 | Blanchard | 23/230 R |
| 4,224,304 | 9/1980 | Sawai et al. | 424/12 |
| 4,268,268 | 5/1981 | Blum | 23/230 B |
| 4,277,560 | 7/1981 | Gray et al. | 435/7 |
| 4,476,231 | 10/1984 | Deindoerfer | 436/534 |
| 4,713,347 | 12/1987 | Mitchell et al. | 436/806 |
| 4,868,131 | 9/1989 | Hiratsuka | 436/528 |
| 4,872,992 | 10/1989 | Oquendo et al. | 210/659 |

Primary Examiner—James C. Housel
Assistant Examiner—William Chan
Attorney, Agent, or Firm—Oblon, Spivak, McClelland, Maier & Neustadt

[57] ABSTRACT

In an analytical method for determining the presene or concentration of analyte in a solution comprising detecting a dissolved detectable substance in solution by passing a solution containing a detectable substance through a detection device for determining the presence of concentration of detectable substance in the solution, the improvement including mixing the solution with one or more particulate reagents to form a suspension, thereby modifying the solution to yield a concentration of total detectable substance which correlates with the concentration of original analyte, and passing the solution through the detecting device. The particles can be used to replace an analyte with a detectable substance or an intermediate which can be reacted in solution to form a detectable substance. Alternatively, the particles can be used to suppress or remove an interfering substance. The apparatus for sample detection includes a continuous flow sample source such as a process liquid source, carrier liquid-injected sample separator column such as an ion exchange column or chromatographic column, or a capillary zone electrophoresis sample separator. It also includes detector for detecting dissolved sample species, connecting apparatus including a flow pasageway communicating with the sample source and detector, a particulate reagent reservoir for reagant particles having a particle size of less then 2 microns, and a flow control communicating with the reservoir and with the flow passageway for metering particulate reagent flow into the flow passageway. The detector should be capable of detecting dissolved sample species in the presence of a particulate reagent.

11 Claims, 5 Drawing Sheets

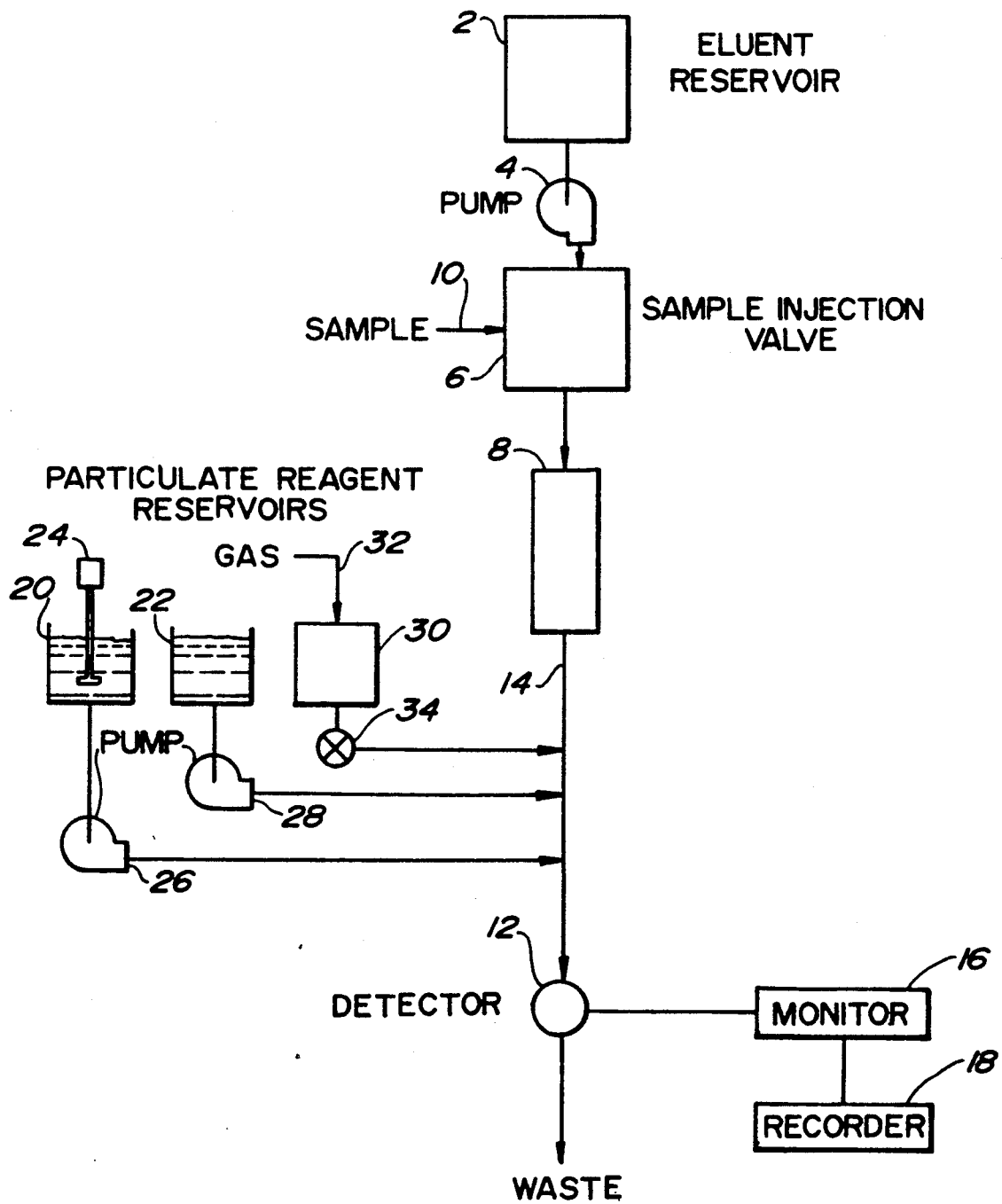
FIG._1

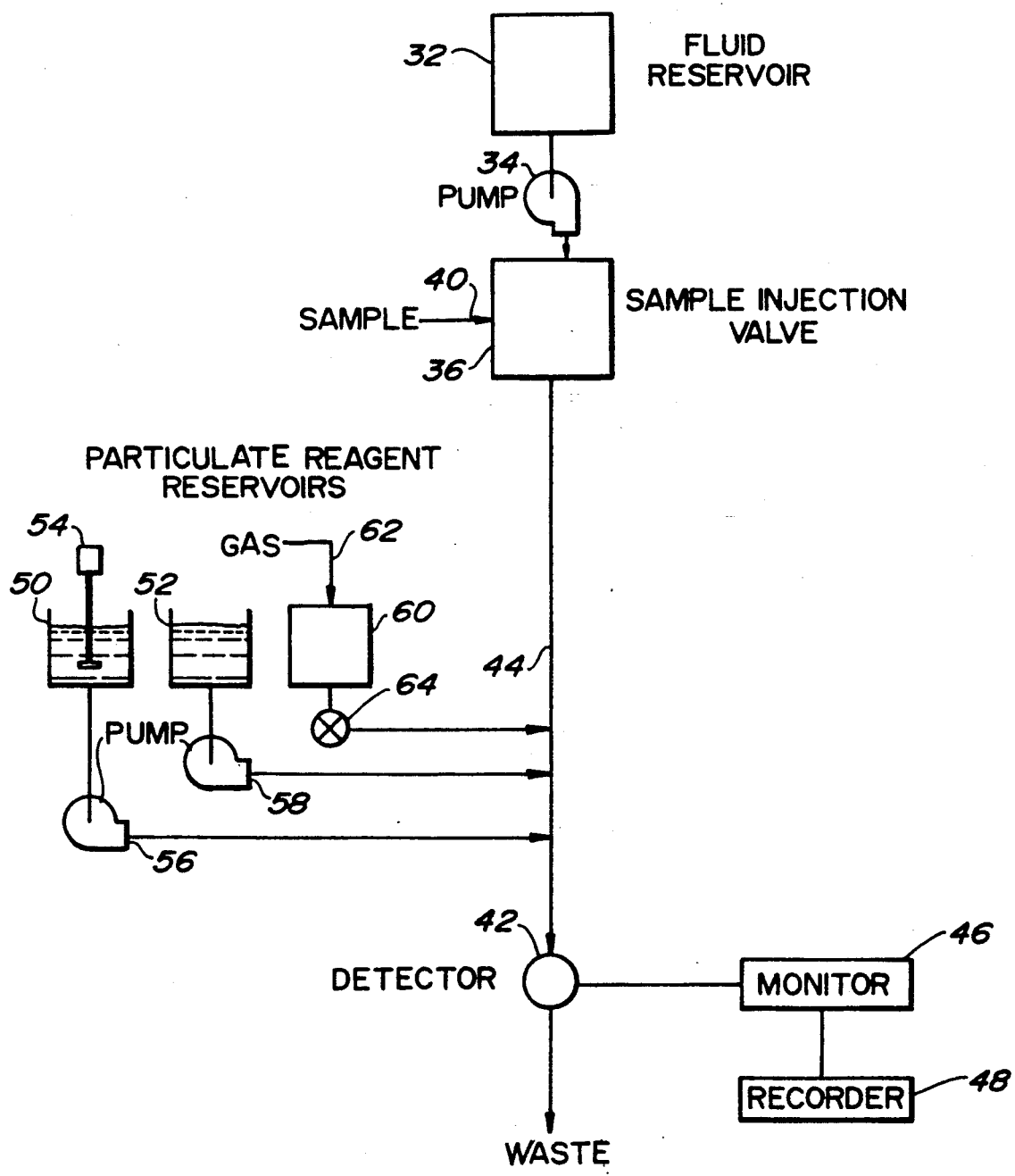
FIG._2

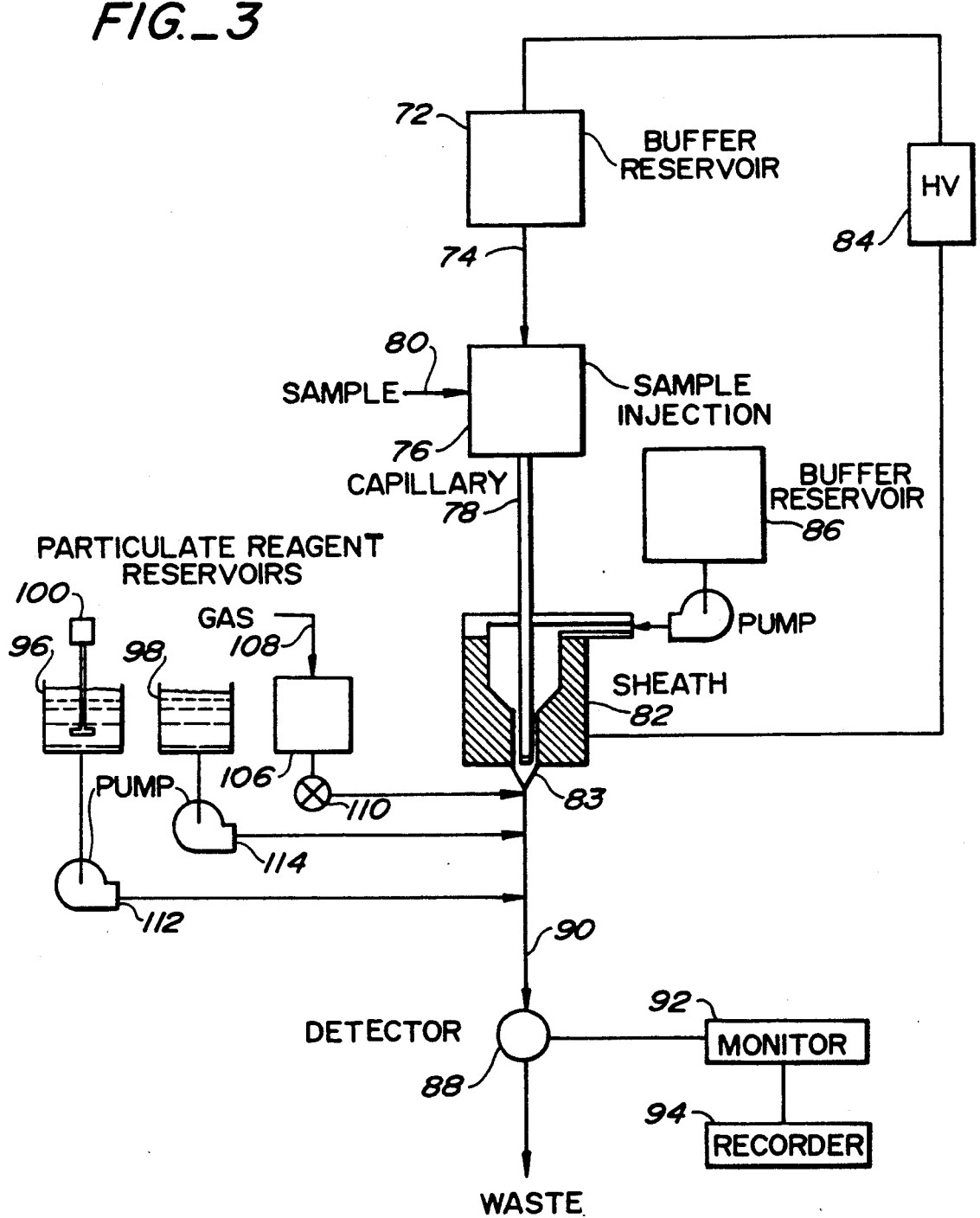
FIG._3

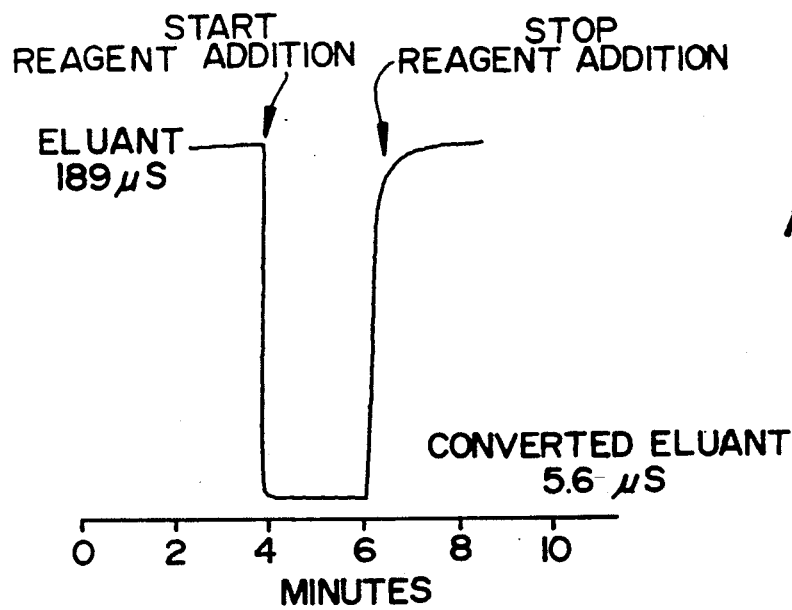
FIG._4
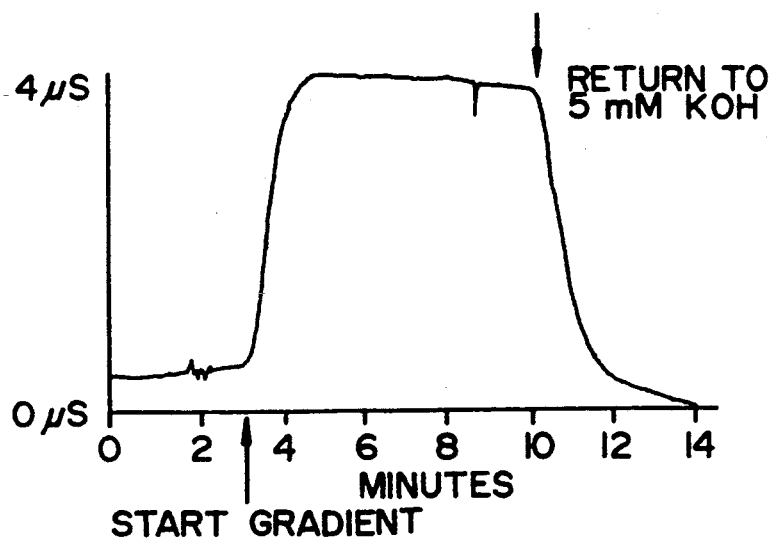
FIG._7
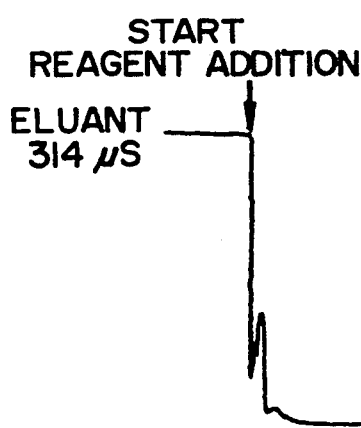
FIG._8

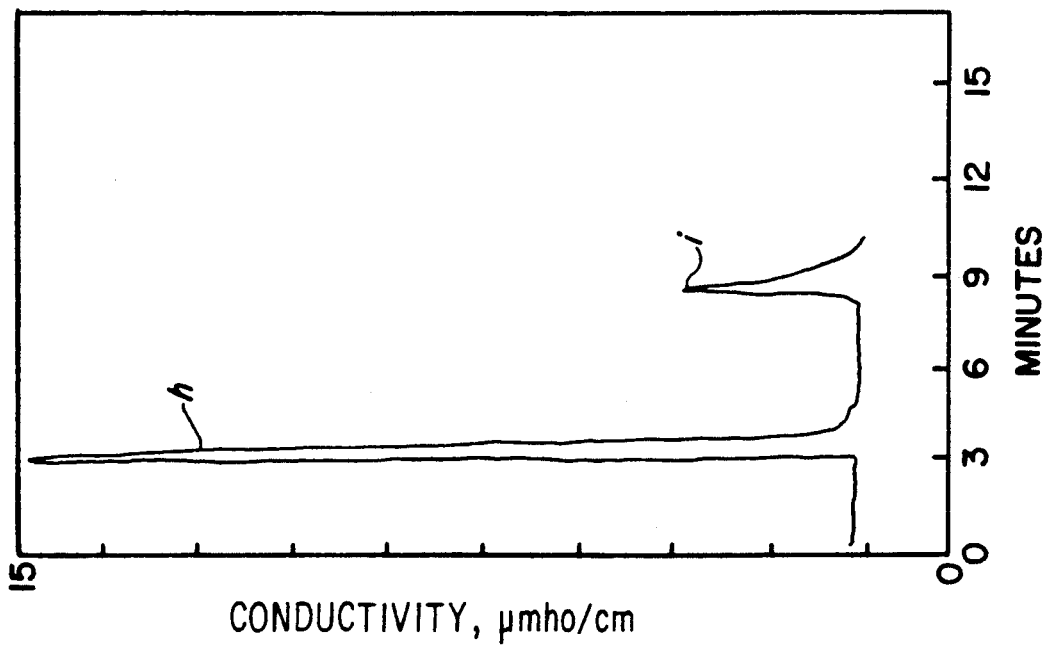
FIG._6.
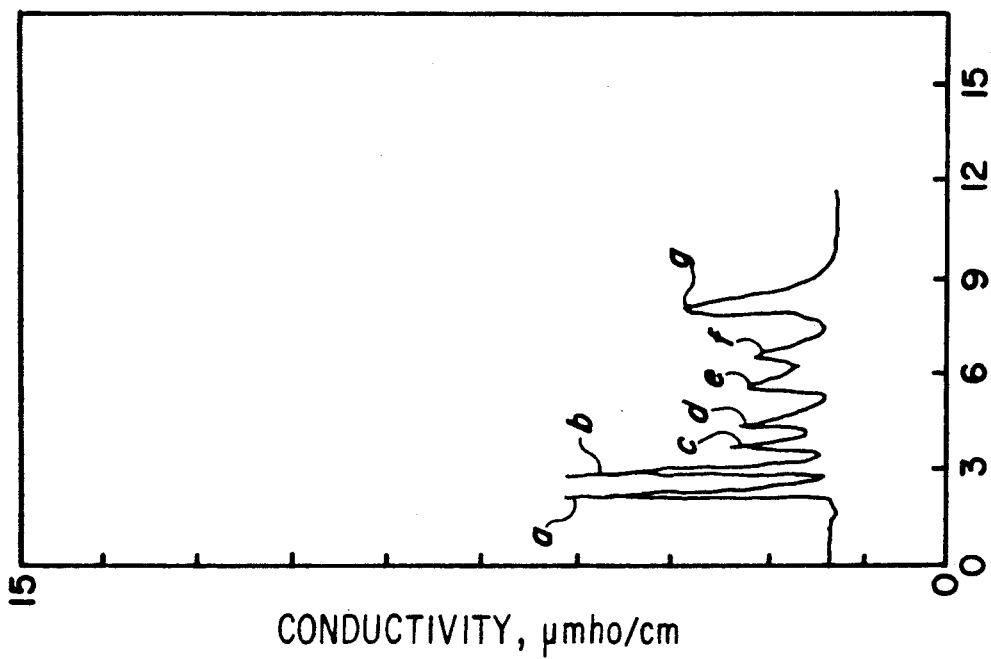
FIG._5.

FLUID ANALYSIS WITH PARTICULATE REAGENT SUSPENSION

RELATIONSHIP TO COPENDING APPLICATION

This application is a continuation-in-part of copending application Ser. No. 07/204,073 filed on Jun. 8, 1988 now abandoned.

FIELD OF THE INVENTION

This invention relates to an apparatus and method for the analytical detection and measurement of one or more dissolved components of a flowing liquid stream, e.g., chromatographic effluent, flow injection analysis stream, or capillary zone electrophoresis stream. In particular this invention relates to a novel apparatus and method for treating a liquid analyte stream prior to its passage through a detector comprising adding particulate reagents to the stream to form a suspension or slurry, or a colloidal dispersion, the insoluble particulate reagents effecting a change in the liquid stream promoting detection of one or more selected dissolved detectable substances in the stream.

1. Background of the Invention

Major advances in flowing stream analytical processes and systems have been made in recent years. The scope and variety of analytes which are successively detected in flowing streams, the accuracy of concentration measurements of analytes, and the reliability of the systems have established flow analytical procedures as essential analytical tools in research, process control, pollution control, and many other fields.

In these processes, a liquid containing a detectable moiety is passed through a detector, and the presence and concentration of the moiety is determined as the flow continues. Three of the most highly developed of these procedures are known as liquid chromatography including HPLC (high performance liquid chromatography), ion chromatography, and flow injection analysis. An new technique, CZE (capillary zone electrophoresis) also passes the stream through a detector.

In each method, the detectable substance is concentrated in a stream segment passing through the detector, and the level or concentration within the segment is determined as it passes through the detector. Dispersion of the detectable substance flattens and widens the concentration peak, reducing sensitivity of the method. Dispersion is affected by flow velocities through connective tubing, length of connective tubing, changes in flow cross-section, and many other factors.

For detecting many substances, chemical treatment of the liquid stream containing a segment with concentrated analyte is required before the detection phase. In liquid chromatography, a variety of post-column treatments are often necessary to obtain a desired sensitivity or to obtain a detectable substance from the analyte. The procedures available include adding and mixing chemicals to achieve a chemical reaction, removing or replacing solution components, and other methods. Accommodating these treatments inherently increases dispersion of the concentrated analyte in the liquid stream. This is expressed by Frei et al, "Reaction detectors in HPLC." J. Chromatographic Science. 17:152-159 (1979), wherein the authors state: "the construction of proper reaction detectors comprises a constant struggle against band broadening." In still another recent publication by Jupille, "UV-Visible adsorption derivatization in liquid chromatography." J. Chromatographic Science. 17:160-167 (1979), the authors listed among disadvantages of the design and state of the reactors: "a need for hardware modification (with attendant loss in flexibility); and ... a risk of band broadening due to post-column mixing volume resulting in loss of resolution."

By way of further explanation, the often mentioned problem of avoiding band spreading is interrelated to various factors, among which is the mode of metering reagent. The reagent that is added to the stream usually has at least a small background signal. Any lack in consistency of metering produces fluctuations in reagent concentration in the effluent, which shows up as "noise" in the detector.

The problem is especially severe where highly concentrated reagent is used, since minute fluctuations can produce high background "noise" levels that severely hamper the sensitivity of the detection. While one of the choices of the prior art is to use concentrated reagent to avoid band spreading by sample dilution, the gain may, nevertheless, be offset at least partially by increased background noise levels.

Ingenious systems have been developed to achieve mixing of reagents, permit adequate reaction times, and accomplish various treatments of the solutions with a minimum of dispersion. Until this invention, the most successful solutions to these problems have been systems based on packed bed and membrane reactors.

Packed bed and membrane reactions have continued to present a limiting factor on sensitivity and versatility, however. Packed beds are used in flow analysis processes to replace analyte ions with more detectable ions by ion exchange or gravitational, through simple ion exchange, enzymatic reactions, or reaction of the analyte with chemicals presented by the bed. They are also used to remove or suppress interfering substances in the liquid stream by adsorption, ion exchange, chemical reaction and the like. In the flow of a concentrated analyte stream segment through the fixed bed of particulates or gel in packed bed reactors, the passage of analyte through the bed is attenuated due to the flow dynamics of the fixed bed system. Whereas these interactions and flows are highly effective to achieve separation of analyte in chromatographic separations, they invariably increase dispersion in simple reaction systems.

Some reactions of the stream with the packed bed reactor may form precipitates. These precipitates may cause high resistance to stream flow or even plug the reactor and make the reactor unusable.

Packed bed reactors cannot be used continuously. After bed depletion, the stream treatment process must be interrupted, and then the reactor is either regenerated or replaced.

Membrane reactions involve passage of the analyte stream across a membrane surface, and this is most efficiently achieved in flow detection systems by passing the stream through a tubular membrane or across a sheet membrane. The length of tubing or configuration of the sheet required to achieve a desired membrane reaction causes a further increase in dispersion, however, limiting the usefulness of this procedure. Membrane reactors are fragile and can burst easily. Also, the membrane is easily plugged or fouled with substances that cannot be removed and make the membrane unusable.

2. Description of the Prior Art

U.S. Pat. No. 4,097,328 describes a method for determining a reduced coenzyme wherein the fluorescence of the reduced coenzyme is measured in an aqueous medium in the presence simultaneously of an organic liquid miscible with water and a dispersion of one or more slightly soluble or insoluble substances. The presence and combination of the organic liquid and particles enhances the fluorescence of the reduced coenzyme.

U.S. Pat. No. 4,650,770 describes an immunoassay employing fluorescent particles and absorbent particles, wherein the absorbent particles substantially inhibit fluorescence when bound to the fluorescent particles through specific non-covalent binding. The fluorescence of the insoluble particles is measured.

West German Patent No. DE 2749956 describes an immunoassay using a photometric method of detection with latex polymer reagents. This is a kinetic method which cannot be readily adapted to flowing streams. Japanese Patents Nos. 59171863, 62002163, 62093663, and 62093664 are also directed to kinetic methods, a reading versus time end point with a batch solution, and cannot be readily adapted to flowing stream measurements. Instrument readings of the sample after substantial or complete reaction are generally required. In general, kinetic immunoassays are not useful in flowing stream detection methods of this invention because the kinetic immunological reactions and reactions producing the detectable species are too slow and too specific.

U.S. Pat. No. 4,665,020 describes a flow cytometer measurement of a binding competition immunoassay wherein a liquid sample containing analyte is mixed with reagent antigen coated fluorescent microspheres and larger microspheres coated with an antibody which binds specifically with the antigen. The particle suspension is measured by laser flow cytometer for fluorescent events and light scattering to provide data correlating to the analyte concentration in the sample. This is a specific immunoassay and no chromatographic separation is present. The insoluble fluorescent particles are measured.

East German Patent No. DD 219,873 describes a continuous flow method for determining HF and $FeF_2$/$FeF_3$ wherein an aqueous suspension of MgO is added to the sample. No chromatographic separation is involved, and this method cannot be extended to a chromatographic separation or other stream methods. The reagent is specific for only one compound in the mixture. Furthermore, the MgO is not insoluble, dissolving in the solution during the method.

Canadian Patent No. 1,103,137 describes a titration of an ion exchange colloidal polymer with an oppositely charged colloidal polymer.

Russian Patent No. SU 1,271,561 describes a counterflow addition of an ion exchange slurry in an industrial separation process. No detection of the slurry mixture is involved.

None of the above detection methods use insoluble particles to produce solutions of soluble materials to be detected. The analytical methods generally involve the production of particular particles correlating in concentration to a solution analyte, usually involving insolubilizing analyte, and measurement or determination of the particle products of the process. Other prior art methods used particles to initiate immunological or chemical reactions, and require completion of lengthy reactions before solution analysis can be performed; they cannot be readily adapted to the treatment and detection of a flowing stream. All of the above methods are specific and cannot be adapted to chromatographic methods.

A surface-enhansed Raman spectroscopy technique for HPLC and FIA detection was described by Freeman et al, Applied Spectroscopy 42:456 (1988). This method involves the production of silver particles correlating in concentration to a solution analyte, resulting in the insolubilization of the analyte and the measurement of the particle products of the process.

OBJECTS AND SUMMARY OF THE INVENTION

The object of this invention is to provide an improved apparatus and method for the analytical detection and measurement of dissolved components of a flowing liquid stream characterized by the development of an improved reactor for stream treatment and detection. In particular, the objective of this invention is to provide a detection apparatus and method comprising treating a liquid stream using chemical reagents to which a detector does not respond to reduce detector noise and increase sensitivity.

A further object of this invention to provide a more versatile detection apparatus and method. For example, chemical treatments which would normally form precipitates can be used in conjunction with the apparatus and method of this invention without danger of plugging or fouling the reactor.

It is a further objective of this invention to provide an improved detection method which is continuous and minimizes peak broadening.

It is a still further object of this invention to provide a detection apparatus and method which are more rugged and more easily performed than prior art methods.

One aspect of this invention is an analytical method for determining the presence or concentration of original analyte in a solution. In its broadest form, the method of this invention is an improvement of methods for determining the presence and concentration of one or more analytes in solution by detecting solubilities detectable substance in solutions with a detecting means for determining the presence of concentration of detectable substance in the solution. The improvement comprises mixing the solution with particulate reagent to form a suspension, the particulate reagent modifying the solution to yield a concentration of total detectable dissolved substance which correlates with the concentration of original analyte; and detecting the detectable dissolved substance in the solution to determine the presence and concentration of the detectable dissolved substance. The method is preferably not an immunoassay.

The particulate reagent can interact with the analyte in a variety of ways to yield a corresponding concentration of total detectable substance in the solution. The particles can comprise dispersible ion exchange particles having an exchangeable ion which is displaced by the analyte for a second substance, the concentration of the second substance correlating with the concentration of analyte originally in the solution. The second substance can be a detectable substance, or alternatively, the second substance can react with reagent in the solution to provide a detectable substance in a concentration which correlates with the concentration of analyte. The particulate reagent can comprise particles which chemically or enzymatically react with the analyte to yield a reaction product which is either a detectable substance or which can be converted by reaction with reagent in the solution to provide a detectable substance.

In a preferred embodiment, the method is applied to analytical methods involving flowing streams of analyte solution. A solution of a detectable substance is passed as a flowing stream through the detecting means to determine the presence and concentration of the detectable dissolved substance in the solution, and the particulate reagent is added to the flowing stream prior to the detection step.

In one embodiment, the solution contains an interfering substance and the particulate reagent interacts with the interfering substance to reduce its level in the solution by ion exchange, chemical reaction, enzymatic reaction adsorption, or absorption. In another embodiment, the solution analyte is converted by interaction with one or more particulate reagents to replace the analyte with a detectable dissolved substance, as by ion exchange, enzymatic action, chemical reaction, etc. prior to the detection step. A combination of these methods can also be applied.

Preferably, the particulate reagent remains in the solution passing through the detecting means. Suitable particulate reagents can be an ion exchange material, chelating material, chemical reactant, adsorbent, absorbent, particles having enzymes bound thereto, or particles having binding partners for interfering substances bound thereto, for example. Particles having, bound thereto, antibodies, antibody binding fragments, or antigens selected for specific antibody binding reactions are not preferred.

Another aspect of this invention is the HPLC, FIA and CZE apparatus for sample detection comprising a sample means for separating or introducing sample species, a detector means for detecting dissolved sample species, and connecting means including a flow passageway communicating with the sample means and detector means. The improvement comprising a particulate reagent reservoir means for reagent particles having a particle size of less than 2 microns, and flow control means communicating with the particles reagent reservoir and with the connecting means flow passageway for metering particulate reagent flow into the flow passageway. The detector means is a means for detecting dissolved sample species in the presence of a particulate reagent. In one preferred embodiment, the detector is a conductivity meter having electrodes which will not be bridged or obstructed by particulate reagent. In such an embodiment, for example, the electrodes are without pores having a diameter less than 10 times the diameter of the largest particulate reagent particles and the electrodes having a spacing which is at least 2 times the diameter of said particle. In another preferred embodiment, the connecting means flow passageway has an inner diameter at least 10 times the diameter of the largest particulate reagent particle. In still another preferred embodiment, the particulate agent reservoir means includes means for maintaining the particulate reagent in suspension. In still other preferred embodiments, the particulate reagent reservoir means is a pressure container, the pressure container having a pressurized gas inlet means and the flow control means includes a flow control valve or the reservoir is an unpressurized container, and the flow control means includes a metering pump.

BRIEF DESCRIPTION OF THE DRAWINGS

FIG. 1 is a high performance liquid chromatography (HPLC) and ion chromatography (IC) schematic representation of the apparatus of this invention.

FIG. 2 is a flow injection analysis (FIA) schematic representation of the apparatus of this invention.

FIG. 3 is a capillary zone electrophoresis (CZE) schematic representation of the apparatus of this invention.

FIG. 4 shows the effect of adding particulate reagent to a carbonate/bicarbonate eluant described in Example 1.

FIG. 5 and FIG. 6 are chromatograms described in Example 1.

FIG. 7 shows the effect of adding particulate reagent to a hydroxide eluant gradient described in Example 3.

FIG. 8 shows the effect of adding particulate reagent of a chloride eluant described in Example 10.

DETAILED DESCRIPTION OF THE INVENTION

This invention is an analytical apparatus and method for determining the presence or concentration of original analyte in a solution. The method comprises an essential step of passing a solution containing a detectable substance through a detecting means for determining the presence or concentration of detectable substance in the solution. The improvement of this invention comprises mixing the solution with particulate reagent to form a suspension, the particulate reagent modifying the solution to yield a concentration of total detectable dissolved substance which correlates with the concentration of original analyte; and passing the solution through the detecting means which determines the presence and/or concentration of the dissolved detectable substance in the solution. This method is not a binding pair assay such as an immunoassay wherein reagent particles are modified by interaction with analyte in solution to effect a change in the reagent particles, and wherein the particle characteristics then are measured. The apparatus is an apparatus in which this method can be effected.

The apparatus and method of this invention are particularly advantageous for post-column treatment of liquid chromatographic eluant streams prior to detection measurement. The automatic detection of sample peaks as they elute from a liquid chromatographic column is necessary for fast, high performance separations. Hence, high performance liquid chromatography (HPLC) is often characterized by the type of detectors which are used. The most common detector for liquid chromatography is the spectrophotometer. Many organic compounds absorb strongly at the UV wavelengths. However, many compounds cannot be detected by this detector. Thus, there have been a multitude of different types of detectors developed for HPLC including amperometric, conductometric, fluorometric and refractometric detectors and the like.

The need for sensitivity and sample selectivity has led to the development of post-column derivatization techniques. Several schemes have also been developed. The most simple post-column reactions involve only the addition of energy in the form of heat, irradiation or electrons. Most other post-column reactions involve the addition of substances such as color-forming reagents or enzymes to react with sample species in the eluant stream.

These reagents have been added to the post-column eluant in essentially three ways. One approach has used solid packed bed column reactors. The reactor contains a reagent that reacts with the sample species and makes the peaks detectable. As the reagent is used, the column reactor must be replaced or regenerated. Another method of post-column derivatization has involved adding reagent dissolved in a solvent using a mixing tee. This approach has limited usefulness because many derivatization require the use of insoluble reagents. Also, other chemicals (such as a counter ion) that may interfere with the detection process may be present in the dramatization reagent. The last method for post-column addition of a reagent uses a membrane such as those use din ion chromatography. The membrane allows the passage of selected reagents to the eluant stream. However, the membranes ar fragile, have a limiting surface area, and can be used only for certain reactions.

This invention introduces an apparatus and a new post-column treatment which are particularly useful in liquid chromatography. Insoluble solids are added post-column to the eluant stream. The solids are dispersed in the eluant and treats the eluant to make the sample peaks detectable. Prior to this invention, addition of solids to liquid chromatographic streams has been avoided. Usually HPLC solvents are filtered to remove all particles over 0.2 microns to extend column life and prevent plugging of the HPLC tubing detector cells.

A schematic representation of the HPLC and IC apparatus of this invention is shown in FIG. 1. The eluent reservoir 2 is connected by tubing and metering pump 4 through sample injection valve 6 to the inlet of the separation column 8. The sample injection valve 6 has a sample inlet means such as a conduit 10. The outlet of separation column 8 is connected to a detector such as a conductivity cell 12 by conduit 14. The detector is connected with a conventional monitor 16 and recorder 18.

The particulate reagent reservoirs can be used to introduce one or more particulate reagents into the liquid stream flowing through conduit 14. Reagent reservoirs 20 and 22 are unpressurized containers. Reservoir 20 is equipped with a stirrer 24 which maintains non-colloidal particles in suspension. Flow control from these reservoirs is maintained by metering pumps 26 and 28 which can be peristaltic pumps, for example. Reagent reservoir 30 is a pressurized container equipped with a gas inlet 32 for pressurized gas and a metering valve 34 to control liquid flow to the conduit 14. Other details and modifications of the apparatus will become apparent from the description provided hereinafter.

A solid reagent is added as a slurry or suspension post-column to the liquid chromatography stream 14 and dispersed in the stream to make a sample/solid flowing suspension. To avoid obstruction of the conduit 14, the conduit diameter should be at least 10 times the diameter of the largest particles of the particulate reagent. The solid treats the eluant to make the sample peaks detectable by either adding a component to the stream, extracting a component from the stream, or by performing both functions sequentially or simultaneously. The treatment may be applied to the entire eluant or to liquid segments containing concentrated analyte. However, because the treatment reagent is an insoluble solid, it does not interfere significantly with many detection processes.

Many types of detectors 12 can be used in the apparatus and method. Many detector transducers respond only to the liquid portion of a suspension, the dispersed solids being "transparent" to the detector and not significantly affecting the measurement. Examples of such detectors include conductometric, amperometric, and potentiometric detectors. Other detectors, such a fluorometric and spectrophotometric detectors can be modified to measure the appropriate property of the dissolved detectable substances in the presence of a dispersed solid. Where the presence of suspended solids interfere in an unavoidable way, the solids can be removed, for example, by filtration with a low dispersion filter such as a tangential flow-through filter before sample detection.

The detectors should not have flow restrictions or electrical element placement which could be obstructed or bridged by the largest particles of the particulate reagent. Some flow-through conductivity meters are not suitable for the larger particles, for example, because their pore size is less than 10 times the largest particle diameter. In general, flow-through porous electrode lonductivity meters are not preferred. Other porous, high surface area working electrodes may also be obstructed. Since the particulate reagents can conduct electricity, a conductivity electrode spacing, for example, which is not at least 2 times the largest particle diameter may be bridged and shorted by the larger particles. Care should be exercised that the detector selected can be used with the particular particulate reagent to be used in the method.

ION CHROMATOGRAPHY

Ion-exchange chromatography is the separation of substances by their differential migration on an ion-exchange column or on a sheet impregnated with an ion exchanger. The sample ions are moved down or eluted form the column with an eluant solution. This is accomplished through the competition of eluant ions and sample ions that react with functional groups on the ion exchanger. The reactions are reversible, so that as a sample ion travels down a column, it will normally "stick" and "unstick" several times. The ability of a sample ions to compete with the eluant ions depends on the characteristics of the ion exchanger and each particular species of sample ion. The affinity of the sample ion for the exchanger is unique, thus providing a basis for performing separations of ion mixture solutions into sequential eluant segments, each containing a single ion species.

Examples of ion chromatography procedures, apparatus, post-column treatment techniques, detection systems, and ion exchange materials are described by Gjerde et al in ION CHROMATOGRAPHY. (2nd Ed.) New York: Dr. Alfred Huthig Verlag (1987), the entire contents of which and the publications cited therein being hereby incorporated by reference. The method of this invention can be applied to all types of ion chromatography.

In anion exchange separations, the cations in a basic eluant containing an alkaline substance such as sodium hydroxide can be suppressed by treatment with particulate cation exchange resin in hydrogen form, for example. In a double suspension application of the invention, the eluant cation suppression is combined with treatment with a second particulate reagent which converts the analyte species into a common species to provide a uniform molar response in the detection step. This can be achieved, for example, by mixing the stream with a particulate anion exchange polymer which replaces the anionic analyte ions with a common anion by ion exchange. In a still further alternative, the double suspension treatment technique can be combined with a treatment with a particulate reagent which masks sample peaks so that minor components can be determined. A particulate silver-form cation exchanger can be used to mask chloride ions in a nitrite ion determination, for example. Also barium-form cation exchange particles can be used to mask sulfate ions in a sulfuric acid trace anion determination.

In cation exchange separations, the anions in an acidic eluant containing an acid substance such as hydrochloric acid an be suppressed by treatment with particulate anion exchange resin in hydroxide form. This is useful for separation of alkali metal ions, alkaline earth metal ions and amines. In a double suspension treatment application of the invention, the eluant anion suppression is combined with treatment with a second particulate reagent which converts the analyte species into a common species to provide a uniform molar response in the detection step. This can be achieved, for example, by mixing the suspension with a particulate cation exchange resin which replaces the cationic analyte ions with a common cation by ion exchange. For transition metal containing eluants, lead ions in the eluant can be suppressed by treatment with a sulfate-form anion exchange resin slurry. The sulfate anions in sulfuric acid eluants can be suppressed by treatment with a lead-form or barium-form cation exchange resin slurry. In a still further alternative, the double suspension treatment technique can be combined with a treatment with a particulate reagent which masks sample peaks so that minor components can be determined. For example, the eluant can be treated with a chelating ion exchange resin slurry to remove transition metals in alkaline earth metal ion determinations.

In ion exclusion procedures, the method of this invention can be used to suppress the chloride ion in hydrochloric acid eluants with a silver-form cation exchange resin slurry. A weak organic acid eluant can be suppressed with a large-ammonium cation-form cation exchange resin slurry.

In mobile phase ion chromatography, a quaternary ammonium hydroxide eluant can be suppressed with a hydrogen-form cation exchange resin slurry.

Removal of the particulate reagent is unnecessary for many ion chromatography detectors such as amperometric, coulometric, potentiometric, fluorescence, and reflectance spectrophotometric detectors, although combination slurries may be required to suppress or remove eluant ions or convert a sample analyte to a detectable form.

In some instances, removal of particulate reagents may be necessary for spectrophotometric (UV-VIS), atomic emission and atomic absorption detectors, for example.

HIGH PERFORMANCE LIQUID CHROMATOGRAPHY

HPLC methods, reagents, apparatus, detection systems, and post-column treatments are described by Krull (editor) in REACTION DETECTION IN LIQUID CHROMATOGRAPHY. New York: Marcel Dekker (1986), the entire contents of which and the publications cited therein being hereby incorporated by reference.

Applying the method of this invention, organic solvent eluant can be removed by particulate adsorbates such as the silicate material absorbent SILICALITE ® (Union Carbide). Particulates supporting chemical reactants and enzymes can be used for chemical reaction of the sample, for example enzyme oxidation or reduction. Ion pairing reagents can be removed by the procedures described above with regard to ion chromatography for masking peaks.

As with the ion chromatography detectors, removal of the particulate reagent is unnecessary for many HPLC detectors such as amperometric, coulometric, potentiometric, fluorescence, and reflectance spectrophotometric detectors. In some instances, removal of particulate reagents may be necessary for spectrophotometric (UV-VIS), atomic emission and atomic absorption detectors, for example.

CONTINUOUS FLOW ANALYSIS, FLOW INJECTION ANALYSIS, AND PROCESS MONITORS

These methods also involve the flow of a sample stream through a detector. Continuous flow analysis with segmented steams and flow injection analysis are described together with the equipment, reagents and detectors therefor by Ruzicka et al in FLOW INJECTION ANALYSIS. New York: John Wiley (1981), the entire contents of which and the references cited therein being hereby incorporated by reference. Continuous flow analysis and flow injection analysis involve the injection of a sample liquid in a flowing carrier stream of a suitable liquid.

In applying the method of this invention to these detection procedures, the particulate reagent is added to the liquid to either convert the sample analyte into a detectable form, convert a sample matrix to a more uniform form, or remove or mask interfering components of the liquid. Many of the procedures correspond to those described above with respect to Ion Chromatography or HPLC. Organic solvents can be removed with SILICALITE ®, the particles can support enzymes or reagents which reduce the background matrix; can support chemical reactants which convert the sample analyte to a form which is more detectable; adjust the pH of the sample, for example, using a weak base or weak acid ion exchange material; and/or replace sample analyte with a common species. The detectors and special considerations required therewith are as described above.

A schematic representation of the FIA apparatus of this invention is shown in FIG. 2. The fluid reservoir 32 is connected by tubing and metering pump 34 through sample injection valve 36 to the inlet of conduit 44. The sample injection valve 36 has a sample inlet means such as a conduit 40. Conduit 44 leads from the sample injection valve outlet to a detector such as a conductivity cell 42. The detector is connected with a conventional monitor 46 and recorder 48.

The particulate reagent reservoirs can be used to introduce one or more particulate reagents into the liquid stream flowing through conduit 44. Reagent reservoirs 50 and 52 are unpressurized containers. Reservoir 50 is equipped with a stirrer 54 which maintains non-colloidal particles in suspension. Flow control from these reservoirs is maintained by metering pumps 56 and 58 which can be peristaltic pumps, for example. Reagent reservoir 60 is a pressurized container equipped with a gas inlet 62 for pressurized gas and a metering valve 64 to control liquid flow to the conduit 44. Other details and modifications of the apparatus will become apparent from the description provided hereinafter.

A solid reagent is added as a slurry or suspension to the liquid stream 44 and dispersed in the stream to make a sample/solid flowing suspension. To avoid obstruction of the conduit 44, the conduit diameter should be at least 10 times the diameter of the largest particles of the particulate reagent. The solid treats the eluant to make the sample peaks detectable by either adding a component to the stream, extracting a component form the stream, or by performing both functions sequentially or simultaneously. The treatment may be applied to the entire liquid stream or to liquid segments containing concentrated analyte. However, because the treatment reagent is an insoluble solid, it does not interfere significantly with many detection processes.

Many types of detectors 42 can be used in the apparatus and method. Many detector transducers respond only to the liquid portion of a suspension, the dispersed solids being "transparent" to the detector and not significantly affecting the measurement. Examples of such detectors include conductometric, amperometric, and potentiometric detectors. Other detectors, such a fluorometric and spectrophotometric detectors can e modified to measure the appropriate property of the dissolved detectable substances in the presence of a dispersed solid. Where the presence of suspended solids interfere in an unavoidable way, the solids can be removed by filtration with a low dispersion filter such as a tangential flow-through filter before sample detection.

The detectors should not have flow restrictions or electrical element placement which could be obstructed or bridged by the largest particles of the particulate reagent. Some flow-through, porous-electrode, conductivity meters are not suitable for the larger particles, for example, because their pore size is less than 10 times the largest particle diameter. In general, flow-through, porous-electrode flow, conductivity meters are not preferred. Other porous, high surface area working electrodes such as those used in coulometric detectors, may also be obstructed. Since the particulate reagents can conduct electricity, a conductivity electrode spacing, for example, which is not at least 2 times the largest particle diameter may be bridged and shorted by the larger particles. Care should be exercised that the detector selected can be used with the particular particulate reagent to be used in the method.

CAPILLARY ZONE ELECTROPHORESIS

Capillary zone electrophoresis (CZE) is a new technique for the separation of ionic species. The technique is characterized by excellent mass sensitivity, low sample consumption, and high resolution. A high potential is applied across a separation capillary tube. Samples introduced at one end of the capillary migrate down the tube based on their ionic mobility. Ions with the highest mobility elute first from the capillary and lowest mobility ions elute last. Because of the combined action of electroosmotic flow with electophoretic separation, all species normally travel in one direction, allowing detection of positively charged, neutral, and negatively charged species at one end of the capillary tubing.

A regulated direct current high voltage power supply provides up to 30 kV potential. These voltages generate microampere currents through the capillary tube. Heat generated by the technique is dissipated through the capillary wall.

Fused silica is most commonly used for electrophoretic capillaries, although PTFE and polyethylene have also been used. Inner diameters of 50–100 microns, with a wall thickness of less than 200 microns are used in most applications. Capillary lengths of 50–100 cm are most frequently used.

Review articles on CZE have been written by Ewing et al, Anal. Chem. 61:292A (1989) and by Gordon et al, Science. 242: 224 (1988).

A schematic representation of the CZE apparatus of this invention is shown in FIG. 3. The buffer reservoir 72 is connected by tubing 74 through sample injection device 76 to the inlet of the separation capillary 78. The sample injection device 76 has a sample inlet means such as a conduit 80. The outlet of the separation capillary 78 is connected to a sheath 82. Buffer reservoir 72 and sheath 82 are in electrical contact with a high voltage source 84 which causes sample ions to migrate down separation capillary 78. Electrical contact of sheath 82 and separation capillary 78 is maintained with buffer pumped from buffer reservoir 86. The outlet 83 of sheath 82 is connected to a detector such as a conductivity cell 88 by conduit 90. The detector is connected with a conventional monitor 92 and recorder device 94.

The particulate reagent reservoirs can be used to introduce one or more particulate reagents into the liquid stream flowing through conduit 90. Reagent reservoirs 96 and 98 are unpressurized containers. Reservoir 96 is equipped with a stirrer 100 which maintains non-colloidal particles in suspension. Flow control from these reservoirs is maintained by metering pumps 112 and 114 which can be peristaltic pumps, for example. Reagent reservoir 106 is a pressurized container equipped with a gas inlet 108 for pressurized gas and a metering valve 110 to control liquid flow to the conduit 90. Other details and modifications of the apparatus will become apparent from the description provided hereinafter.

A solid reagent is added as a slurry or suspension post-column to the liquid stream 90 and dispersed in the stream to make a sample/solid flowing suspension. To avoid obstruction of the conduit 90, the conduit diameter should be at least 10 times the diameter of the largest particles of the particulate reagent. The solid treats the eluant to make the sample peaks detectable by either adding a component to the stream, extracting a component from the stream, or by performing both functions sequentially or simultaneously. The treatment may be applied to the entire eluant or to liquid segments containing concentrated analyte. However, because the treatment reagent is an insoluble solid, it does not interfere significantly with many detection processes.

All of the detectors that work for HPLC, IC, and FIA methods can also be used for CZE. However CZE flow rates are usually significantly less than other techniques. CZE detector and tubing void volumes are adjusted accordingly.

NON-FLOWING STREAM SAMPLE PREPARATION

The methods of this invention are also useful for treating liquid samples which are not flowing streams, for example, standard batch analytical methods wherein a dissolved detectable species is determined with a standard analytical detector. In general, the particles used in the methods of this invention remain in suspension during the detection step and are used to effect the changes described above for the flowing stream methods. Specific applications include pH adjustment of a sample with an appropriate ion exchange particle slurry; masking, for example with a chelating ion exchange resin slurry; and adsorption of contaminants, for example with a high surface area, non-polar solid to absorb organic components but not inorganic components of the solution. The detectors and special considerations required therewith are as described above with flowing stream methods.

PARTICULATE REAGENTS

Particulate reagents can be inorganic or organic. Inorganic reagents can be based on, for example, alumina, silica or molecular sieve materials. Organic reagents can be polymers, for example cross-linked forms of polystyrene, polyesters, polyamides, and cellulose. Depending on the application, the particulate reagent can be used directly for adsorption or absorption reactions or alternatively, the particulate reagent can contain a reaction group on the solid substrate. The reaction group is chemically bound or adsorbed to the particles and therefore is also immobile and insoluble. The functional or reaction group can be ion exchange, partition, affinity, ligand exchange, enzyme, catalyst, chelating, complexing, and the like.

Although usually sized too large for application in this invention, particulate reagents of the same chemical form are available from a number of manufacturers. Alumina, silica and silica derivatives, and molecular sieves particles are well known and available from many sources.

Ion exchange polymers are most useful as particulate reagents in the methods of this invention. Conventional ion exchange resin particles can be used, and their composition and method of manufacture are well known in the art. They also are widely available from commercial sources. Useful ion exchange resins are described by Kunin, ION EXCHANGE RESINS. New York: Wiley (1958). The provision of reaction groups can be provided on the monomer prior to polymerization or can be coupled with the polymer bead after emulsion or suspension polymerization.

Commercial polymer beads usually have a size of 10 or more microns and are too large for use in this application. The size of organic and inorganic particles can be reduced sing standard, well known grinding techniques using mils which were specially designed for grinding paint pigments, cosmetic powders, and other materials. However, the grinding techniques must be selected to avoid introductions of impurities which would result in a detector background signal. Reagent particles can also be purified using ultra filtration techniques.

Recently, submicron polymer particulate reagents have become available from Interfacial Dynamics, Fastek, and Seragen Diagnostics, Inc. companies. The methods for production of these reagents are described by Bangs in UNIFORM LATEX PARTICLES. Seragen Diagnostics, Inc. (Indianapolis, Ind., 1984). However, the high size uniformity provided by these particulate compositions is not required in the method of this invention.

The particulate reagents used in the process of this invention should preferably form a stable or slow-settling colloidal suspension. The particles should have an average size below 2 microns and preferably have a size from about 100 angstroms up to 0.2 microns. Optimally, the particles should be colloidal in size. Uniform size is not necessary except in methods where the light reflection might interfere with the detection process.

A new experimental sulfonated low crosslinked latex polystyrene is available from Rohm and Haas Co. (Philadelphia, Pa.). The material, XE 391, is a 0.2 micron average particle size with a range of about 0.1 to 0.3 microns. The material is normally supplied as a 10% suspension.

The concentration of particles used in the selection is selected to satisfy the required interactions. For many reactions, the concentration is dependent upon the surface area of the reagent particles, the finer the particle size, the lower the concentration required. In general, any amount can be used which does not interfere with the free flow of solution in the flow systems and does not foul the equipment. For particles having a size less than 0.1 microns, a concentration up to about 20 weight percent can be used. An amount of less than about 5 weight percent is preferred.

PERFORMANCE OF A SULFONATED POLYSTYRENE SUSPENSION PARTICULATE REAGENT 10 ml of a 1.00% suspension of a less than 1 micron sulfonated cation exchanger was added to 50 ml of deionized water and titrated with 0.0200M NaOH. The progression of the titration was followed with pH (Orion Research Model 301 pH meter) and conductivity (Wescan Model 213A) measurements. Capacity of the cation exchanger particulate reagent was 2.3 mequiv/g dry weight. The conductance of deionized water was 1.22 microSiemens.

TABLE 1

| Titrant, mL | pH | MicroSiemens |
|---|---|---|
| 0.00 | 3.90 | 2.50 |
| 2.00 | 4.00 | 2.55 |
| 4.00 | 4.10 | 2.55 |
| 6.00 | 4.20 | 2.45 |
| 8.00 | 4.40 | 2.30 |
| 9.00 | 4.50 | 2.20 |
| 10.00 | 4.70 | 2.10 |
| 10.50 | 4.90 | 1.95 |
| 11.00 | 5.10 | 1.90 |
| 11.40 | 5.40 | 1.90 |
| 11.60 | 5.60 | 2.00 |
| 11.80 | 6.00 | 2.05 |
| 12.00 | 6.50 | 2.25 |
| 12.20 | 8.80 | 2.55 |
| 12.40 | 9.20 | 2.85 |
| 12.60 | 9.40 | 3.20 |
| 12.80 | 9.50 | 3.45 |
| 13.00 | 9.55 | 3.70 |
| 13.20 | 9.60 | 5.10 |
| 13.40 | 9.65 | 6.50 |
| 13.60 | 9.70 | 8.40 |
| 13.80 | 9.75 | 12.2 |
| 14.00 | 9.80 | 17.8 |
| 14.50 | 9.85 | 27.2 |
| 15.00 | 9.95 | 36.5 |
| 16.00 | 10.10 | 53.5 |
| 17.00 | 10.20 | 71.6 |
| 18.00 | 10.30 | 88.3 |
| 19.00 | 10.40 | 104 |
| 20.00 | 10.40 | 119 |

The suspension reduced the conductivity of about 13 mL of NaOH titrant. As the titrate is added to the suspension, the conductivity of the suspension at first is reduced up to about 12 mL of titrant. This shows that the sulfonated particulate reagent has a low background conductance that is further reduced as the reagent is converted to the lower conducting sodium form.

This invention is further illustrated by the following specific but non-limiting examples. Temperatures are given in degrees centigrade and concentrations as weight percents unless otherwise specified. Procedures which are constructively reduced to practice herein are described in the present tense, and procedures which have been carried out in the laboratory are set forth in the past tense.

EXAMPLE 1

Ion Chromatography

This example demonstrates a method suitable for separating and quantifying several inorganic anions, specifically fluoride, chloride, nitrite, bromide, nitrate, phosphate, and sulfate, at concentrations, for example, ranging from 1 to 50 ppm. The aqueous mobile phase was a mixture of 0.0028M $NaHCO_3$ and 0.0022M $Na_2CO_3$. The flow rate was 1 mL/min, and the chart recorder rate was 2 min/cm.

The sample mixture was applied to a chromatographic separation column (15 cm × 4 mm) packed with a prototype version of SARASEP® AN1 (Sarasep, Inc., Reno, Nev.), a low-capacity anion exchange resin. After chromatographic separation, the eluant was directed to a mixing tee. The stream was mixed with a 2% suspension of fully sulfonated cation exchange resin having a particle size of less than one micron and in the hydrogen form. The suspension stream flow was 1 mL/min. The mixture including the suspended solid resin was directed through the conductivity cell of a conductivity detector (Model 213A, Wescan Instruments) with a cell constant of 3 $cm^{-1}$. The detector sensitivity was set to 10 microsiemens full scale. The suspension converted the eluant to low conducting carbonic acid by donating hydronium cations to the eluant while at the same time removing sodium cations, and by the same mechanism, converting the sample anions to highly conducting acids.

The effect of adding particulate reagent suspension to the eluant is shown by FIG. 4. The carbonate/bicarbonate eluant has a background conductance of 189 microSiemens. When the suspension was added post-column to the eluant stream, the conductance was lowered to 5.6 microSiemens. Stopping the reagent addition resulted in an immediate return to the original background conductance.

Two chromatograms are shown in the representations of FIG. 5 and FIG. 6. FIG. 5 is the chromatogram obtained with a standard solution containing fluoride (a), chloride (b), nitrite (c), bromide (d), nitrate (e), phosphate (f), and sulfate (g), all of the anions listed above. FIG. 6 represents a separation of Saratoga, CA tap water on Oct. 23, 1987, showing chloride (h) and sulfate (i).

EXAMPLE 2

Ion Chromatography

This example is an extension of the method of Example 1. This detection process combines the first particulate reagent treatment, eluant suppression and sample anion treatment, with a second treatment with a second particulate reagent. This second reagent converts the analyte species into a common species to provide a uniform molar response in the detection step.

The sample mixture is applied to a chromatographic separation column (15 cm × 4 mm) packed with Sarasep® AN1 (Sarasep, Inc., Reno, Nev.), a low-capacity anion exchange resin. After chromatographic separation, the eluant is directed to a mixing tee. The stream is mixed with a 5% suspension of fully sulfonated ion exchange resin having a particle size of less then one micron and in the hydrogen form. The suspension stream flow is 0.5 mL/min. After mixing, the stream is directed to a stream degasser consisting of a small bore silicon tube surrounded by vacuum. The degassed stream is directed to a second mixing tee. The stream is mixed with a 5% suspension of fully functionalized strong base anion exchange resin having a particle size of less than one micron and in the chloride form. The second suspension stream flow is 0.5 mL/min. The suspension mixture of column effluent and two particulate reagents is directed through a conductivity cell of a conductivity detector (Model 213A, Wescan Instruments) with a cell constant of 3 $cm^{-1}$. The detector sensitivity is set to 10 microSiemens full scale.

The first suspension converts the eluant to a low conducting carbonic acid by donating hydronium cations to the eluant while, at the same time, removing sodium cations. By the same mechanism, the sample anions are converted to highly conducting acids. After the first particulate treatment, the degasser removes the carbonic acid from the stream by diffusion of carbon dioxide through the silicon wall. After removal of the carbonic acid/carbon dioxide, the second suspension treatment converts the sample acids to the common species, highly conducting hydrochloric acid.

EXAMPLE 3

Ion Chromatography

Eluant gradients are used in ion chromatography to increase the strength of the eluant as the chromatographic separation progresses. This allows the faster elution of late eluting ions. However, in order to successfully perform a eluent gradient, the background signal must remain as constant as possible.

A gradient of 5 mM to 50 mM KOH (carbonate not removed) was performed as a step gradient. The eluant (1 mL/min) was mixed with a 1 mL/min flow of a 2% suspension of less than 1 micron fully sulfonated gel-type cation exchanger (Benson Polymeric, Reno, Nev.). The detector was a WATERS MODEL 430 (Millipore, Corp., Milford, Mass.).

FIG. 7 shows the conductance of the eluant stream in the step gradient. A change of only 4 microSiemens conductance was measured. Without the addition of the particulate reagent, the conductance would be 85 microSiemens for the 5 mM KOH and increased to 850 microSiemens as the eluant concentration is increased to 50 mM KOH.

EXAMPLE 4

Ion Chromatography

This example describes the separation and quantification of several strong-acid sample anions—chloride, nitrate and sulfate—in the presence of a weak-acid sample anion, acetate.

The eluant is an aqueous solution of 0.020M phthalic acid having a flow rate of 3.5 mL/min, and the column (10 cm × 4.6 mm) is a low-capacity anion exchanger (Cat. No. 269013, Wescan Instruments).

After chromatographic separation of the sample, the eluant is directed to a mixing tee where it is mixed with a 5% suspension of 0.2 micron, high surface area, macroporous polymer (P 80, poly(styrene-divinyl benzene);

Benson Polymeric, Reno, Nev.). The particulate suspension reagent flow is 1 ml/min. The suspension mixture of column eluant and reagent is directed to the cell of a conductivity reactor (Model 213A, Wescan Instruments). The low pH eluant elutes acetate with the solvent peak, and chloride, nitrate, and sulfate, respectively, are eluted in an 8 minute separation. The suspension reagent adsorbs the non-polar eluant reagent, phthalic acid, from the aqueous solution but does not affect the sample anions which are in the form of highly conducting acetic, hydrochloric, nitric and sulfuric acids.

EXAMPLE 5

Ion Chromatography

This example uses electrochemical amperometric detection. Particulate reagent is used to absorb organic compounds in the sample that might deactivate or poison the working electrode of the detector.

A 10 cm×7.8 mm anion exclusion column (high capacity, sulfonated, 8% cross-linked, poly(styrene-divinylbenzene) resin, Benson Polymeric, Reno, Nev.) is used to separate sulfite in beer. Beer contains organics that may adsorb on the working electrode of a detector. The eluant is aqueous 0.005M sulfuric acid set to a flow rate of 0.85 mL/min. The sulfite sample is injected, and sulfite elutes at about 3.5 min. The column effluent is directed to a mixing chamber where it is mixed with a 1% suspension of 0.1 micron, high surface area (415 $M^2/g$), macroporous poly(styrene-divinylbenzene) resin. Then, the stream is directed to an amperometric detector (Model 271, Wescan Instruments) with a Pt electrode adjusted to +0.6 volts. The particulate reagent adsorbs organics that elute form the column, but does not affect the oxidation and detection of the sulfite ions.

EXAMPLE 6

Ion Chromatography

This example describes the separation and quantification of several common alkali metal cations—lithium, sodium, potassium and ammonium. The aqueous mobile phase is a mixture of 0.003M $HNO_3$ having a flow rate of 2 mL/min.

The sample is directed to a chromatographic separation column (10 cm×3.2 mm) packed with a low-capacity cation exchange resin (Cat. No. 269004, Wescan Instruments). After chromatographic separation, the eluant is directed to a mixing tee where it is mixed with a 1% suspension of 0.2 micron high capacity anion exchanger in the hydroxide form. The suspension stream flow is 1 mL/min. The mixture is directed through the conductivity cell of a conductivity detector (Model 213A, Wescan Instruments). The suspension converts the eluant to low conducting water by removing nitrate anions. The suspension also converts the sample cations to highly conducting bases. The separation is completed in less than 10 min with the sample peaks eluting in the order of lithium, sodium, ammonium and then potassium.

EXAMPLE 7

Ion Chromatography

In principle, the sulfonated particulate reagent can be used to react any salt of a weak acid. As further example, A 1 mL/min stream of 5 mM sodium molybdate was reacted with a 1.1 mL/min stream of 2% suspension of fully sulfonated cation exchange particulate reagent. The conductance (Wescan Model 213A) of the eluant was measured before and after reaction with particulate reagent.

TABLE 2

| | Conductance (microSiemens) | |
|---|---|---|
| | before reaction | after reaction |
| sodium molybdate, 5 mM | 299 | 95 |

The final conductance is due to molybdic acid. Anions of strong acids separated with this eluant would be detected as acids.

EXAMPLE 8

Ion Chromatography

In this example, suspended particulate reagent is used to mask the presence of a potential interfering metal.

Magnesium and calcium are separated on a 10 cm×3.2 mm low capacity cation exchanger (Benson Polymeric, Reno, Nev.). The eluant is aqueous-based, made up with 0.001M ethylene diamine adjusted to pH 7 with nitric acid and is adjusted to a flow rate of 1.5 mL/min. A sample containing a 100 fold molar excess of iron (II), and 0.001M each of magnesium and calcium are injected and separated on the column. The column effluent is directed to a mixing tee where it is mixed with a chelating particulate reagent. The particulate reagent consists of a 0.1 micron 1% suspension of poly(styrene-divinylbenzene) particles. The polymer is high capacity with iminodiacetate functional groups in the sodium form. The reagent complexes with the iron that elutes form the column, thus preventing interference with the magnesium peak. The suspension/column effluent stream is directed to a conductivity detector, and the magnesium and calcium separation is recorded in a 6 min chromatogram.

EXAMPLE 9

Ion Chromatography

In this example, ion chromatography is used to separate transition metals. The hydroxide suppressor particulate reagent cannot be used for these metal cations, as it is used for the alkali metals of Example 4, because hydroxide precipitates some transition metals and thus prevents them from being detected.

Copper (II), Nickel (II), zinc (II), and cadmium (II) are separated on a 15 cm×4.0 mm low capacity, cation exchange column (Benson Polymeric, Reno, Nev.). The mobile phase is 0.005M $BaCl_2$ at a flow rate of 1.5 mL/min. The sample is injected, and the metal ions eluted in the order: copper, nickel, zinc, and cadmium. As the metals elute from the column, the column effluent is directed to a mixing tee where it is mixed with a 1% suspension of 0.1 micron high capacity, strong base, cation exchange resin in the sulfate form. The particulate reagent suspension stream flow is 1 ml/min. After reaction, the stream is directed to a conductivity detector (Model 213A, Wescan Instruments).

The suspension reagent converts the eluant to low conducting water by precipitating the barium cation with the sulfate on the reagent. Metal cations are detected as the metal sulfates.

EXAMPLE 10

Ion Chromatography

Low molecular weight organic acids are separated by ion exclusion chromatography. In this example, oxalic, maleic, malic, succinic, formic and acetic acids are separated on a glass lined column (30 cm × 7.8 mm) packed with a fully sulfonated styrene-divinylbenzene copolymer (Polymeric resin Cat. No. 825, Benson Polymeric, Reno, Nev.). The eluant is 0.003N HCl at a flow rate of 0.7 mL/min. After the separation of the organic acids, the eluant is directed to a mixing tee where it is mixed with a suspension of 0.2 micron high capacity cation exchange resin in the silver form. The suspension stream flow is 1 mL/min. The mixture is directed through the conductivity cell of a conductivity detector (Model 213A, Wescan Instruments). The suspension converts the eluant to low conducting water by precipitating the chloride anion with the silver cation on the particles. The suspension does not affect the organic acid analytes. The separation is completed in less than 12 min with the sample peaks eluting in the order oxalic, maleic, malic, succinic, formic and acetic acids.

An example of precipitation of a chloride containing eluant with a Ag-form cation exchange less than 1 micron particulate suspension was performed. A stream of 10 mM NaCl was treated with a 2% suspension. FIG. 8 shows the conductance without treatment was 314 microSiemens (Model 213A, Wescan Instruments). After treatment, the stream conductance decreased to 2.9 microSiemens.

EXAMPLE 11

HPLC

In this example, HPLC is used to separate and detect anionic surfactants, i.e., alkyl benzene sulfonates. The mobile phase is made with 0.01N $(NH_4)_3B_{10}O_{16} \cdot 8H_2O$ (ammonium borate) and 0.01M boric acid to produce an aqueous mobile phase having a pH of 8.3. The retention of anionic surfactant is controlled by varying acetonitrile concentration in the mobile phase while retaining the boric acid and ammonium borate levels at constant concentrations. Gradient elution is used with the acetonitrile concentration varied from 50% to 90%. The flow rate is 1.5 mL/min. The HPLC reverse phase column is (15 cm × 4.6 mm) is packed with with 5 micron silica-based, reversed phase bonded material (ULTRASPHERE-IP ®, Beckman Corporation). The suspension detection solution is a 5% aqueous suspension of 0.2 micron completely sulfonated styrene-divinylbenzene copolymer beads in the hydrogen form. The suspension solution is added post-column and directed to a reaction loop before flowing to a conductivity detector. The suspension reagent converts the eluant to weakly conducting boric acid while converting the sample peaks to highly conducting alkyl sulfonic acids.

EXAMPLE 12

HPLC

In this example, several amines are separated on a polymeric reverse phase column using an ion pairing reagent. Methylamine, dimethylamine, and trimethylamine are separated on a 25 cm × 4.6 mm column containing 10 micron, macroporous, hydrophobic, reverse phase packing (Polymeric P 80, Benson Polymeric). The eluant is a 20:80 methanol/water solution of the ion pairing reagent, 0.005M octanesulfonic acid. The sample is injected, and the amines eluted over a ten minute period. The column effluent is directed to a mixing tee where it is mixed with a 1% 0.1 micron suspension of particulate reagent consisting of a high capacity anion exchange resin in the borate form. Then the stream is directed to a conductivity detector. The borate particulate reagent converts the ion pairing reagent to low conducting boric acid and converts the sample amines to highly conducting ammonium borate compounds.

EXAMPLE 13

Flow Injection Analysis

In this Example, the ionic content of a sample is measured. The sample is injected into a stream containing a mixture of two particulate reagents. One particulate reagent is a 1%. 0.1 micron, high capacity polymeric cation exchange resin in hydronium form. The other reagent is a 1%, 0.1 micron, high capacity anion exchange resin in the chloride form. The reagent converts the cations in the sample to hydronium ions, and converts the anions in the sample to chloride ions. The streams containing the sample is directed to a conductivity detector (Model 213A Wescan Instruments). The suspension reagent stream has very little background conductivity. The sample is converted to hydrochloric acid, and the peak height is proportional to the ionic content of the original sample.

EXAMPLE 14

Capillary Zone Electrophoresis

A separation of several alkali metals are performed by capillary zone electrophoresis. Samples containing ions were dissolved in a buffer solution consisting of 20 mM morpholinoethanesulfonic acid (MES) adjusted by histidine to pH 6.1. The separation of rubidium, potassium, sodium, and lithium is performed in 8 minutes in a 60 cm, 75 micron inside diameter, fused-silica capillary. The applied voltage is 15 kV . The cations elute form the capillary in the order stated above and are directed to a mixing sheath. A particulate reagent suspension of anionic exchanger in hydroxide-form is added to the sample stream and the mixture is directed to a conductivity detector. The particulate suspension takes up the buffer acid salt while converting the sample cation counter anion to hydroxide. The cations are detected as high conducting bases in the presence of low conducting organic base.

I claim:

1. In an analytical method for determining presence or concentration of original analyte in a solution comprising detecting a detectable dissolved substance in solution with a detecting means for determining the presence or concentration of the dissolved substance, the improvement comprising
    a) mixing the solution with particulate reagent to form a flowable suspension, the particulate reagent modifying the solution to yield a concentration of total detectable substance which correlates with the concentration of original analyte while remaining insoluble, wherein the particulate reagent does not have bound thereto, an antibody, antibody binding fragment, or antigen selected for specific antibody binding reactions; and
    b) detecting the presence or concentration of the detectable dissolved substance in the solution with the detecting means.

2. The method of claim 1 for determining presence or concentration of original analyte in a solution, wherein the detection step is performed by passing the solution through the detecting means.

3. The method of claim 2 wherein the particulate reagent interacts with the analyte to yield a corresponding concentration of total detectable substance in the solution.

4. The method of claim 3 wherein the particulate reagent comprises dispersible ion exchange particles having an exchangeable substance thereon which is displaced by the analyte for a second substance, the concentration of the second substance correlating with the concentration of analyte originally in the solution.

5. The method of claim 4 wherein the second substance is a solubilized detectable substance.

6. The method of claim 3 wherein the second substance reacts with reagent in the solution to provide a detectable dissolved substance in a concentration which correlates with the concentration of analyte.

7. The method of claim 3 wherein the particulate reagent comprises particles which chemically or enzymatically react with the analyte to yield a reaction product which is either a detectable substance or which can be converted by reaction with dissolved or particulate reagent in the solution to provide a detectable substance.

8. The method of claim 1 wherein the solution contains an interfering substance and the particulate reagent interacts with the interfering substance to reduce its level in the solution by ion exchange, chelation, chemical reaction, enzymatic reaction, adsorption, or absorption.

9. The method of claim 1, 2, 3, 4, 5, 6, 7 or 8, wherein the particulate reagent remains in the solution passing through the detecting means.

10. The method of claim 1, 2, 3, 4, 5, 6, 7 or 8 wherein said particulate reagent is selected from the group consisting of ion exchange materials, chemical reactants, adsorbents, absorbents, and particles having enzymes abound thereto.

11. The method of claim 1, 2, 3, 4, 5, 6, 7 and 8 wherein the analyte solution is mixed with a plurality of said particulate reagents.

* * * * *